United States Patent [19]

Clausen et al.

[11] Patent Number: 5,409,503
[45] Date of Patent: Apr. 25, 1995

[54] OXIDATION HAIR DYE WITH A CONTENT OF 5-AMINOPHENYL DERIVATIVES, PROCESS FOR OXIDATIVE DYEING OF HAIR AND NEW 5-AMINOPHENOL DERIVATIVES

[75] Inventors: Thomas Clausen; Wolfgang R. Balzer, both of Alsbach; Helmut Keller, Darmstadt, all of Germany

[73] Assignee: Wella Aktiengesellschaft, Darmstadt, Germany

[21] Appl. No.: 140,769

[22] Filed: Oct. 21, 1993

Related U.S. Application Data

[63] Continuation of Ser. No. 777,548, Jan. 9, 1992, abandoned.

[30] Foreign Application Priority Data

May 31, 1990 [DE] Germany .................. 40 17 516.2

[51] Int. Cl.$^6$ ............... A61K 7/13; C07C 211/28; C07C 211/29
[52] U.S. Cl. ............... 8/408; 8/405; 8/406; 8/407; 8/412; 8/421; 564/442; 564/443
[58] Field of Search ............... 8/405, 406, 407, 408, 8/412, 421, 424; 564/443, 442

[56] References Cited

U.S. PATENT DOCUMENTS

| | | |
|---|---|---|
| 3,738,799 | 6/1973 | Kalopissis et al. ............... 564/443 |
| 4,006,185 | 2/1977 | Tobin et al. ............... 564/442 |
| 4,976,742 | 12/1990 | Rose et al. ............... 8/421 |
| 5,015,260 | 5/1991 | Tamura et al. ............... 8/408 |
| 5,180,396 | 1/1993 | Grollier et al. ............... 8/406 |
| 5,180,397 | 1/1993 | Grollier et al. ............... 8/407 |

Primary Examiner—Paul Lieberman
Assistant Examiner—Caroline L. Dusheck
Attorney, Agent, or Firm—Michael J. Striker

[57] ABSTRACT

The composition for oxidative dyeing of hair contains 0.01 to 5.0 percent by weight of at least one 5-aminophenol compound of the formula

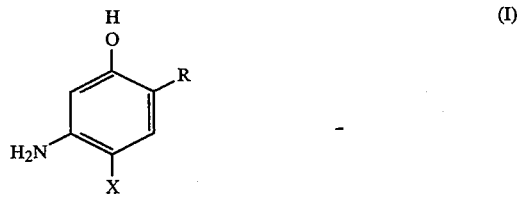

wherein R is an alkyl group having 1 to 4 carbon atoms, X is fluorine or $OR^1$ and $R^1$ is an alkyl group having 2 to 4 carbon atoms, a monohydroxyalkyl group with 2 to 4 carbon atoms or a dihydroxyalkyl group with 3 and 4 carbon atoms, and physiologically tolerated water-soluble salts thereof as coupler substance; and 0.1 to 6.1 percent by weight of a total amount of the coupler substance and at least one developer substance. The developer substance can be 1,4-diaminobenzene, 2,5-diaminotoluene, 2,5-diaminobenzyl alcohol, 2-(2'-hydroxyethyl)-1,4-diaminobenzene, 4-aminophenol, 4-amino-3-methylphenol, 4-amino-2-methoxymethylphenol, 4-amino-2-ethoxy-methylphenol and tetraaminopyrimidine and physiologically tolerated water-soluble salts thereof. The invention also concerns certain new substituted 2-alkyl-5-aminophenols including 5-amino-4-ethoxy-2-methylphenol, 5-amino-4-(2'-hydroxyethyl)oxy-2-methylphenol and 5-amino-2-ethyl-4-fluorophenol.

19 Claims, No Drawings

OXIDATION HAIR DYE WITH A CONTENT OF 5-AMINOPHENYL DERIVATIVES, PROCESS FOR OXIDATIVE DYEING OF HAIR AND NEW 5-AMINOPHENOL DERIVATIVES

This is a continuation of application Ser. No. 07/777,548 filed Jan. 9, 1992, now abandoned.

The subject matter of the invention is a composition and a process for the oxidative dyeing of hair based on 5-aminophenol derivatives as coupler substances, as well as new 5-aminophenol derivatives.

BACKGROUND OF THE INVENTION

Oxidative dyestuffs have achieved considerable importance in the area of hair dyeing. The dyeing is brought about in the hair shaft by the reaction of certain developer substances with suitable coupler substances in the presence of an oxidizing agent.

Numerous special requirements are set for oxidative dyestuffs which are used for dyeing human hair. For example, they must be unobjectionable in toxicological and dermatological respects and must enable the desired dyeing intensity. Favorable fastness to light, permanent waving, acids and rubbing are required of the achievable hair colorings. But such hair colorings must in every instance remain stable over a period of at least 4 to 6 weeks without being affected by light, rubbing or chemical agents. Moreover, it is necessary that a wide assortment of different color shades can be produced by combining suitable developer and coupler components.

1,4-diaminobenzene, 2,5-diaminotoluene, 3-methyl-4-aminophenol and p-aminophenol in particular are used as developer substances. Resorcinol, 4-chlororesorcinol, 2-methylresorcinol, 2,4-diaminoanisole, m-phenylenediamine, 1-naphthol and m-aminophenol are preferably used as coupler substances.

Resorcinol and m-aminophenol are preferably used as coupler substances in combination with p-phenylenediamine or 2,5-diaminotoluene as developer substances to achieve natural tones. In so doing, the yellow cast produced by resorcinol is compensated for by the addition of m-aminophenol so that warmer tones are obtained. The m-aminophenol is suitable for use as coupler component in oxidation hair dye compositions for producing fashionable tones, especially fashionable red tones, only under certain conditions, since it produces inadequate dyeing with respect to coloring intensity with p-aminophenol or its derivatives.

Hair dye compositions containing m-aminophenol derivatives as coupler substances are known from DE-OS 38 17 710. An example of such an aminophenol derivative is 3-amino-4-methoxyphenol. However, the latter is auto-oxidizable and, with p-phenylenediamines as developer substances, produces weak blue to violet coloring. No dyestuff is formed under the usual oxidative conditions with p-aminophenols as developer substances and 3-amino-4-methoxyphenol as coupler component.

Further, 5-amino-4-chloro-2-methylphenol, as coupler substance for oxidative hair dye compositions, is known from DE-OS 35 24 329. 5-amino-4-chloro-2-methylphenol leads to coloring in the red range whose dyeing intensity and red component are not satisfactory.

SUMMARY OF THE INVENTION

It is an object of the present invention to provide compositions for the oxidative dyeing of hair containing a coupler substance which, in combination with developer substances such as p-aminophenol or its derivatives, leads to hair coloring of high color intensity in the red range and is suitable for shading fashionable red tones.

The subject matter of the present patent application is therefore a composition for the oxidative dyeing of hair based on a combination of developer substances and coupler substances, characterized in that it contains at least one 5-aminophenol derivative of the general formula

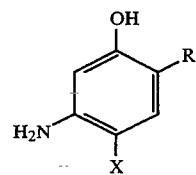

(I)

as coupler substance, in which R is an alkyl group with 1 to 4 carbon atoms and X is fluorine or the group $OR^1$, $R^1$ being an alkyl group with 2 to 4 carbon atoms, a monohydroxy alkyl group with 2 to 4 carbon atoms or a dihydroxy alkyl group with 3 to 4 carbon atoms or its physiologically tolerated water-soluble salt. Chloride, sulfate, phosphate, propionate, lactate and citrate are examples of physiologically tolerated water-soluble salts.

The compounds 5-amino-4-fluoro-2-methylphenol, 5-amino-4-ethoxy-2-methylphenol, 5-amino-4-(2'-hydroxyethyl)oxy-2-methylphenol and 5-amino-2-ethyl-4-fluorophenol are particularly suitable for use in these hair dye compositions.

The subject matter of the present patent application is also new 5-aminophenol derivatives of the general formula

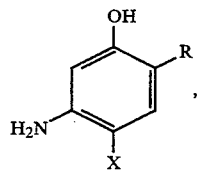

(II)

in which R is an alkyl group with 1 to 4 carbon atoms and X is fluorine or the group $OR^1$, $R^1$ being an alkyl group with 2 to 4 carbon atoms, a monohydroxy alkyl group with 2 to 4 carbon atoms or a dihydroxy alkyl group with 3 to 4 carbon atoms, provided that R is not methyl if X is fluorine.

Examples of compounds of formula (II) according to the invention are 5-amino-2-ethyl-4-fluorophenol, 5-amino-4-ethoxy-2-methylphenol and 5-amino-4-(2'-hydroxyethyl)oxy-2-methylphenol.

The 5-aminophenol derivatives of the general formula (I) (which include the new 5-aminophenol derivatives of the formula (II)) can be produced in a generally applicable production process according to the following reaction scheme (II), in which R and $OR^1$ have the designations indicated above and the mesyl group is understood as an example for a possible protective group, based on the 4-fluoro-2-alkylphenols.

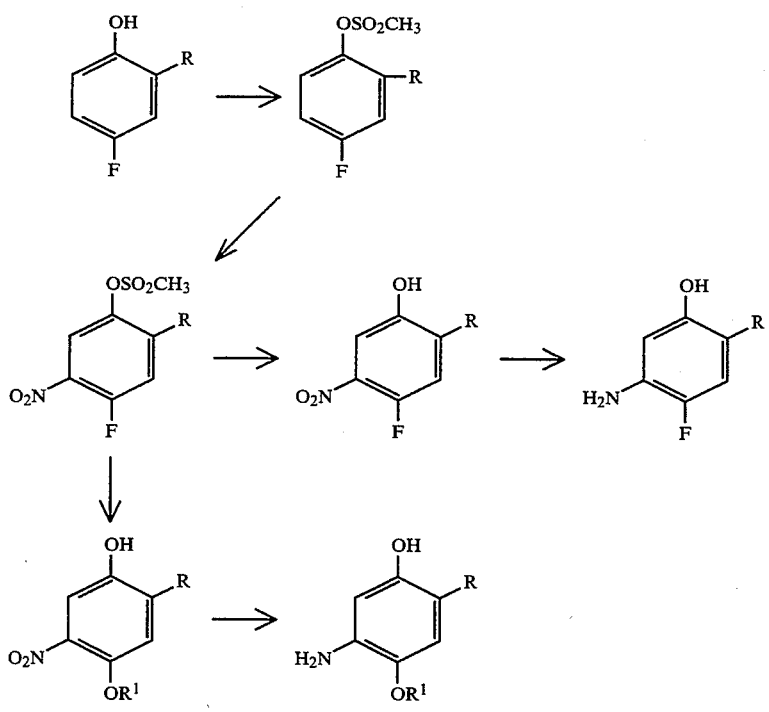

III

The 4-fluoro-2-alkylphenols are first nitrated with nitric acid in sulfuric acid after prior introduction of a suitable protective group, e.g. a mesyl group for the hydroxy group. The protective group is split off in an acidic or alkaline medium, with a strong base in the case of the mesyl group, and produces 4-fluoro-5-nitro-2-alkylphenols which are then hydrogenated to form the 5-amino-4-fluoro-2-alkylphenols of the general formula (I). The hydrogenation is carried out, e.g. in alcoholic solution, with the addition of a suitable catalyst, e.g. palladium. The 5-amino-4-alkoxy-2-alkylphenols, 5-amino-4-monohydroxyalkoxy-2-alkylphenols and 5-amino-4-dihydroxyalkoxy-2-alkylphenols of the general formula (I) are obtained by conversion of the 4-fluoro-5-nitro-2-alkylphenols with a highly alkaline solution of the corresponding alcohol, e.g. methanol, ethanol, ethylene glycol, and subsequent hydrogenation with the addition of a suitable catalyst.

The 5-aminophenol derivatives of the general formula (I) are coupler substances which are eminently suitable for dyeing hair in combination with suitable developer substances.

Intensive hair coloring in the red range can be produced with the compounds of formula (I) in combination with developer substances, e.g. p-aminophenol or its derivatives. The achieved coloring has a clearly higher red component in a tone which, moreover, has a higher color saturation than the coloring achieved with the conventionally used coupler substances 3-aminophenol or 5-amino-2-methylphenol.

The very good dyeing properties of the hair dye composition containing the compounds of the general formula (I) become apparent in that this composition enables a dyeing of graying hair which is not chemically damaged beforehand easily and with good covering power.

The coupler substance of formula (I) is to be contained in the hair dye composition in a quantity of 0.01 to 5.0 percent by weight, preferably 0.1 to 3.0 percent by weight.

The coupler substance of formula (I) is generally used in approximately molar quantities with respect to the utilized developer substances. However, it is not disadvantageous if the proportion of coupler substance exceeds or falls below that of the developer substance, although equimolar use has proven advisable. Further, it is not necessary that the developer components and coupler components constitute uniform products, rather the developer component can be a mixture of known developer substances and the coupler component can be a mixture of the compounds, according to the invention, of the general formula (I) and known coupler substances.

Particularly the following known coupler substances, alone or in combination or their physiologically tolerated water-soluble salts, are taken into consideration as constituents of the hair dye composition according to the invention: 1-naphthol, resorcinol, 4-chlororesorcinol, 4,6-dichlororesorcinol, 2-methylresorcinol, 2-amino-4-(2'-hydroxyethyl)aminoanisole, 2,4-diaminobenzyl alcohol, m-phenylenediamine, 2,4-diamino-1-(difluoromethoxy)benzene, 5-amino-2-methylphenol, 2,4-diaminophenoxyethanol, m-aminophenol, 3-amino-4-chloro-6-methylphenol, 3-amino-2-methylphenol, 4-amino-2-hydroxy-phenoxyethanol, 4-hydroxy-1,2-methylenedioxybenzene, 4-(2'-hydroxyethyl)amino-1,2methylenedioxybenzene, 2,4-diamino-5-ethoxytoluene, 4-hydroxyindole, 3-amino-5-hydroxy-2,6-dimethoxypyridine and 3,5-diamino-2,6-dimethoxypyridine.

Moreover, the hair dye compositions contain developer substances, particularly 1,4-diaminobenzene, 2,5-diaminotoluene, 2,5-diaminobenzyl alcohol, 2-(2'-hydroxyethyl)-1,4-diaminobenzene, 4-aminophenol, 4-amino-3-methylphenol, 4-amino-2-methoxymethylphenol, 4-amino-2-ethoxymethylphenol and tetraaminopyrimidine or their physiologically tolerated, water-soluble salts. Such oxidative dyestuffs which are known and conventional for hair dyeing are described among others in the book by E. Sagarin, "Cosmetics, Science and Technology" Interscience, Publishers Inc., New York (1957), pages 503 ff. and in the book by H. Janistyn, "Handbook of Cosmetics and Fragrances" [Handbuch der Kosmetika und Riechstoffe] (1973), pages 338 ff. The quantity of developer substances contained in the described hair dye compositions is 0.01 to 5.0 percent by weight, particularly 0.1 to 3.0 percent by weight.

The total quantity of combined developer and coupler substances contained in the hair dye composition described here is to be approximately 0.1 to 6.0 percent by weight, preferably 0.5 to 4.0 percent by weight.

Further, the hair dye compositions can also contain other dyeing components, e.g. the self-coupling dyestuffs 6-amino-2-methylphenol, 2-amino-5-ethoxyphenol and 2-amino-5-methylphenol, as well as other conventional direct-dyeing dyestuffs, e.g. triphenylmethane dyestuffs such as Diamond Fuchsine (C.I. 42,510) and Leather Ruby HF (C.I. 42,520), aromatic nitro dyestuffs such as 2-nitro-1,4-diaminobenzene, 2-amino-4-nitrophenol, 2-amino-5-nitrophenol, 2-amino-4,6-dinitrophenol, 2-amino-5-(2'-hydroxyethyl)aminonitrobenzene and 4-(2'-hydroxyethylamino)-3-nitrotoluene, 1-(2'-ureidoethyl)amino-4-nitrobenzene and azo dyestuffs Acid Brown 4 (C.I. 14,805) and dispersed dyestuffs such as 1,4-diaminoanthraquinone and 1,4,5,8-tetraaminoanthraquinone.

Other suitable dyestuffs which are absorbed directly on the hair are described e.g. in the book by J. C. Johnson, "Hair Dyes" Noyes Data Corp, Park Ridge USA (1973), pages 3–91 and 113–139 (ISBN: 0-8155-0477-2).

The total quantity of aromatic nitro dyes, self-coupling and direct-dyeing dyes, azo and dispersed dyes in the hair dye composition can be 0.1 to 4.0 percent by weight.

Of course, the coupler and developer substances and other dye components mentioned above, insofar as they are bases, can also be used in the hair dye compositions in the form of physiologically tolerated acid addition salts, e.g. as hydrochlorides or sulfates or—insofar as they possess aromatic OH groups—in the form of salts with bases, e.g. as alkali phenolates.

Moreover, other conventional cosmetic ingredients can also be present in the hair dye compositions, e.g. antioxidants such as ascorbic acid, thiogylcolic acid or sodium sulfite, perfume oils, complexing agents, wetting agents, emulsifying agents, thickeners, hair care materials, etc.

The preparation form of the hair dye composition described here can be e.g. an aqueous or aqueous-alcoholic solution. However, a cream, gel or emulsion is particularly preferred as preparation form. Its composition is a mixture of dye components with ingredients conventionally used for such preparations.

Conventional ingredients for the hair dye composition are e.g. solvents such as water, lower aliphatic alcohols, e.g. ethanol, propanol and isopropanol, as well as polyvalent alcohols such as glycol, glycerol and 1,2-propylene glycol, wetting agents or emulsifying agents from the classes of anionic, cationic, amphoteric or nonionic surface-active substances such as fatty alcohol sulfates, ethoxylated fatty alcohols, alkyl sulfonates, alkylbenzene-sulfates, alkyltrimethylammonium salts, alkylbetaines, ethoxylated fatty alcohols, ethoxylated nonylphenols, fatty acid alkanol amides or ethoxylated fatty acid esters, also thickeners such as higher fatty alcohols, starch, cellulose derivatives, vaseline, paraffin oil and fatty acids, as well as hair care materials such as cationic resins, lanolin derivatives, cholesterol, pantothenic acid and betaine.

The aforementioned constituents are used in the hair dye composition in amounts which are conventional for such purposes, for example, the wetting agents and emulsifying agents are used in concentrations of approximately 0.5 to 30 percent by weight, the thickeners are used in quantities of approximately 0.1 to 25 percent by weight and the hair care materials are used in a concentration of approximately 0.1 to 5.0 percent by weight.

Depending on the composition, the hair dye composition according to the invention can react slightly acidic, neutral or alkaline. In particular, they have a pH value in the alkaline range between 8.0 and 11.5. They are preferably adjusted with ammonia. However, organic amines, e.g. monoethanolamine and triethanolamine, or inorganic bases such as sodium hydroxide and potassium hydroxide can also be used.

The subject matter of the invention is also a process for the oxidative dyeing of hair in which the hair dye composition described above is mixed immediately prior to use with a suitable oxidizing agent, particularly hydrogen peroxide, and a quantity of this mixture sufficient for dyeing the hair, generally 60 to 200 g depending on the fullness of the hair, is applied to the hair. The mixture is allowed to act on the hair at 15 to 50° C. for approximately 10 to 45 minutes, preferably 30 minutes, the hair is then rinsed with water and dried. The hair is washed with a shampoo after this rinse, if necessary, and possibly rerinsed with a weak organic acid such as citric acid or tartaric acid. The hair is then dried.

Hydrogen peroxide or its addition compounds in urea, melamine or sodium borate in the form of 3 to 12%, preferably 6% aqueous solutions chiefly come under consideration as oxidizing agents for the development of the hair dye. If a 6% hydrogen peroxide solution is used as oxidizing agent, then the weight ratio between the hair dye composition and the oxidizing agent is 5:1 to 1:2, preferably 1:1. Larger quantities of oxidizing agent are used chiefly when there are higher dyestuff concentrations in the hair dye composition or when a more intensive bleaching of the hair is intended simultaneously.

The following examples explain the subject matter of the invention in more detail without limiting it to the examples.

PRODUCTION EXAMPLES

Example 1: 5-amino-2-ethyl-4-fluorophenol

Step 1: 5-fluoro-2-mesyloxyethylbenzene

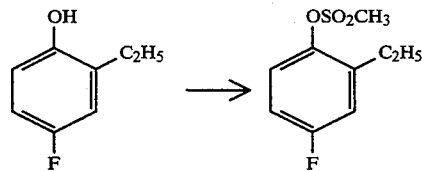

6.27 g (44.79 mmoles) 4-fluoro-2-ethylphenol are dissolved in 6.5 ml pyridine and 6.9 g (60.52 mmoles) mesyl chloride are added by drops accompanied by stirring. After a reaction period of 30 minutes at 50° C., the reaction mixture is poured on ice, extracted with ether and washed with water. 8.98 g (41.20 mmoles, 92% of theory) of a colorless oil with a boiling point of 101° C. at 53.33 Pa are obtained.

$^1$H-NMR (CDCl$_3$): δ=1.25 (t; J=7.5 Hz; 3H; —CH$_2$-CH$_3$)

2.73 (q; J=7.5 Hz; 2H; —CH$_2$-CH$_3$)

3.20 (s, 3H, —SO$_2$CH$_3$)

6.92 (ddd, J$_{5,6}$=8.9 Hz, J$_{5,F}$=8 Hz; J$_{5,3}$=3.1 Hz; 1 H; 5-H)

7.00 (dd, J$_{3,F}$=9.1 Hz, J$_{3,5}$=3.1 Hz; 1 H; 3-H)

7.27 ppm (dd; J$_{5,6}$=8.9 Hz; J$_{6,F}$=4.9 HZ; 1 H; 6-H)

MS (70 EV): m/e=218 (M)

Step 2: 5-fluoro-2-mesyloxy-4-nitroethylbenzene

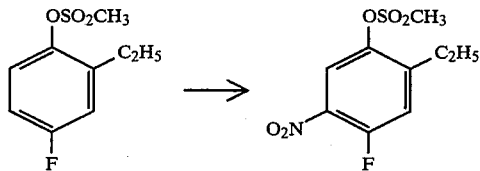

8.72 g (40 mmoles) 5-fluoro-2-mesyloxyethylbenzene are dissolved at 0 degrees Celsius in 45 ml concentrated H$_2$SO$_4$ and mixed with 3 ml concentrated nitric acid at 0 to 5° C. After one hour the reaction mixture is poured on ice water, the precipitate is removed by suction and washed with water to a neutral state. After recrystallization from ethanol, 7.9 g (30 mmoles, 75 percent of theory) of the product are obtained in the form of colorless crystals with a melting point of 68° C.

$^1$H-NMR (DMSO): δ=1.29 (t; J=7.5 Hz; 3 H; —CH$_2$-CH$_3$)

2.83 (q; J=7.5 Hz; 2 H; —CH$_2$-CH$_3$)

3.22 (s; 3 H, —SO$_2$-CH$_3$)

7.24 (d; J$_{3,F}$=11.2 Hz; 1 H; 3-H)

8.04 (d; J$_{6,F}$=6.5 Hz; 1 H; 6-H)

MS (70 EV): m/e=263 (M+)

Step 3: 2-ethyl-4-fluoro-5-nitrophenol

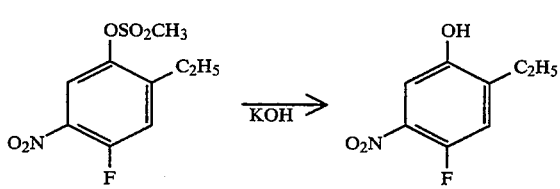

5.26 g (20 mmole) 5-fluoro-2-mesyloxy-4-nitroethylbenzene are added to a solution of 4 g KOH in 200 ml water and heated to 60° C. accompanied by brisk stirring for 30 minutes. After cooling and acidifying° with hydrochloric acid, the reaction mixture is poured on ice and the precipitate is removed by suction. 2.26 g (12.12 mmoles, 61% of theory) the product are obtained in the form of orange-yellow crystals with a melting point of 100 to 102° C.

$^1$H-NMR (DMSO): δ=1.26 (t; J=7.5 Hz; 3 H; —CH$_2$-CH$_3$)

2.67 (q; J=7.5 Hz; 2 H; —CH$_2$-CH$_3$)

5.35 (s; 1H, OH exchanged with D$_2$O), 7.06 (d; J$_{3,F}$=11.6 Hz; 1 H; 3-H)

7.49 ppm (d; J$_{6,F}$=6.2 Hz; 1 H; 6-H)

MS (70 EV): m/e=185 (M+)

Step 4: 5-amino-2-ethyl-4-fluorophenol hemisulfate

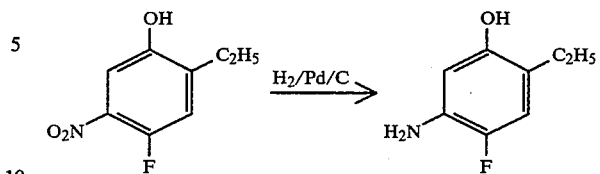

1.95 g (10.53 mmoles) 2-ethyl-4-fluoro-5-nitrophenol are dissolved in 20 l ethanol and hydrated at room temperature over a palladium/carbon catalyst. After the theoretical amount of hydrogen is absorbed, the filtrate is acidified with sulfuric acid and the solvent is sucked off in a vacuum. 1.42 g (9.16 mmoles, 87% of theory) of the crystalline product are obtained which melts at a temperature of 245 to 247° C. accompanied by decomposition.

$^1$H-NMR (DMSO): δ=1.08 (t; J=7.5 Hz; 3 H; —CH$_2$-CH$_3$)

2.45 (q; J=7.5 Hz; 2 H; —CH$_2$-CH$_3$)

6.56 (d; J$_{6,F}$=10.5 Hz; 1 H; 3-H)

6.88 (d; J$_{6,F}$=6.5 Hz; 1 H; 3-H)

7.8 (s; 2 H, NH$_2$ exchanged with D$_2$O), 9.3 ppm (s; 1 H, OH exchanged with D$_2$O)

MS (70 EV): m/e=155 (M+)

Example 2: 5-amino-4-methoxy-2-methylphenol hydrochloride

Step 1: 5-fluoro-2-mesyloxytoluene

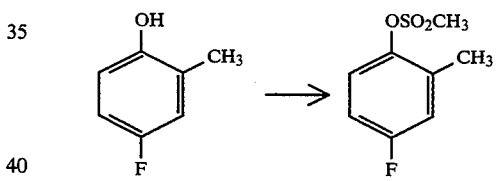

5.64 g (44.76 mmoles) of 4-fluoro-2-methylphenol are dissolved in 6.5 ml pyridine. 6.9 g (60.52 mmoles) mesyl chloride are added by drops accompanied by stirring. After a reaction period of 30 minutes at 50° C., the reaction mixture is cooled, poured on ice and extracted with ether. After washing with water and removing the ether, the residue is distilled in a vacuum. 7.3 g (35.78 mmoles, 90% of theory) of the product with a boiling point of 153 to 155° C. at 1733 Pa and a melting point of 40 to 41° C. are obtained.

$^1$H-NMR (DMSO): δ=2.3 (s; 3 H; Ar-CH$_3$)

3.46 (s; 3 H; —SO$_2$-CH$_3$)

7.13 (m; 1 H; 3-H)

7.24 (d; 1 H; 5-H)

7.37 ppm (m; 1 H, 6-H)

MS (70 eV): m/e=204 (M+)

Step 2: 5-fluoro-2-mesyloxy-4-nitrotoluene

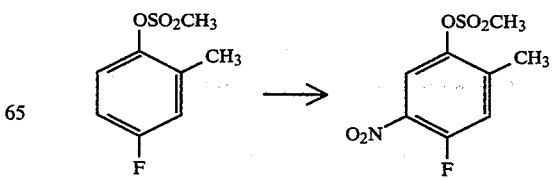

8.16 g (40 mmoles) 5-fluoro-2-mesyloxytoluene are dissolved at 0 degrees Celsius in 45 ml concentrated sulfuric acid and mixed with 3 ml concentrated nitric acid at 0 to 5 degrees Celsius. After one hour the reaction mixture is poured on ice water, the precipitate is removed by suction and washed with water. After recrystallization from ethanol, 7 g (28.4 mmoles, 71 percent of theory) of the product are obtained in the form of yellow crystals With a melting point of 97° C.

$^1$H-NMR (CDCl$_3$): δ=2.46 (s; 3 H; ArCH$_3$)
3.31 (s; 3 H; —SO$_{22}$-CH$_3$ )
7.24 (d; J=11 Hz; 3-H)
8.02 ppm (d; J=6 Hz, 6-H)
MS (70 eV): m/e=249 (M+)

Step 3: 4-methoxy-2-methyl-5-nitrophenol

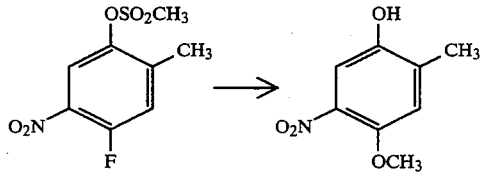

2.3 g (9.24 mmoles) 5-fluoro-2-mesyloxy-4-nitrotoluene are dissolved in a solution of 1.3 g KOH in 5 ml water and 50 ml methanol and stirred at room temperature for 16 hours. The concentrated residue is absorbed in dichloromethane and chromatography is effected with silica gel in dichloromethane. 0.84 g (4.25 mmoles, 46 % of theory) of the product are obtained in the form of dark-yellow crystals with a melting point of 82 to 84° C.

$^1$H-NMR (CDCl$_3$): δ=2.32 (s; 3 H; ArCH$_3$)
3.91 (s; 3 H; O-CH$_3$)
5.33 (s (wide); 1 H; OH exchanged with D$_2$O)
6.87 (s; 1 H; 3-H)
7.41 ppm (s; 1 H; 6-H)
MS (70 eV): m/e =183 (M)

Step 4: 5-amino-4-methoxy-2-methylphenol hydrochloride

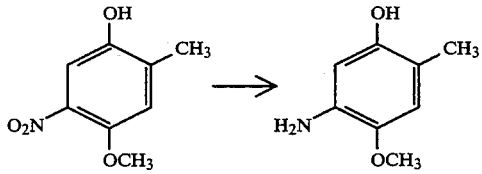

1.8 g (9.84 mmoles) 4-methoxy-2-methyl-5-nitrophenol are dissolved in 20 ml ethanol and hydrated at room temperature over palladium/carbon. After the theoretical amount of hydrogen is absorbed, the catalyst is removed by filtration and the filtrate is acidified with hydrochloric acid. After the solvent is removed, 1.35 g (8.02 mmoles, 90 of theory) of the product are obtained in the form of reddish-brown crystals which melt at 248° C. accompanied by decomposition.

$^1$H-NMR (D$_6$—DMSO): δ=2.1 (s; 3 H; Ar-CH$_3$)
3.76 (s; 3 H; OCH$_3$)
6.94 (s; 1 H; 3-H)
7.01 (s; 1 H; 6-H)
9.5 (s; 1 H; OH; exchanged with D$_2$O)
10.10-10.03 ppm
(s; 2 H; NH$_2$; exchanged with D$_2$O)
MS (70 eV): m/e=153 (M+)

Example 3: 5-amino-4-ethoxy-2-methylphenol

Step 1 and Step 2: see Example 2

Step 3: 4-ethoxy-2-methyl-5-nitrophenol

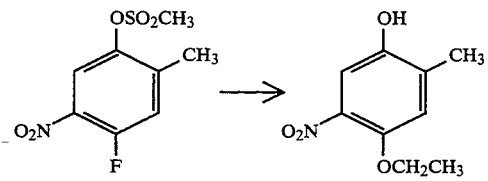

2.3 g (9.24 mmoles) of 5-fluoro-2-mesyloxy-4-nitrotoluene are dissolved in a solution of 1.3 g KOH in 5 ml water and 50 ml ethanol and stirred for 16 hours at room temperature. The concentrated residue is absorbed in dichloromethane and chromatography is effected with silica gel in dichloromethane. 0.6 g (3.01 mmoles, 31% of theory) of the product are obtained in the form of dark-yellow crystals with a melting point of 81° C.

$^1$H-NMR (CDCl$_3$): δ=1.42 (t; J=6.9 Hz; 3 H; OCH$_2$-CH$_3$)
2.29 (s; 3 H; ArCH$_3$)
4.11 (q; 3 =J=6.9 Hz; 2 H, OCH$_2$-CH$_3$)
5.39 (s (wide); 1 H; OH; exchanged with D$_2$O)
6.85 (s; 1 H; 3-H)
7.36 ppm (s; 1 H; 6-H)
MS (70 eV): m/e=197 (M+)

Step 4: 5-amino-4-ethoxy-2-methylphenol hydrochloride

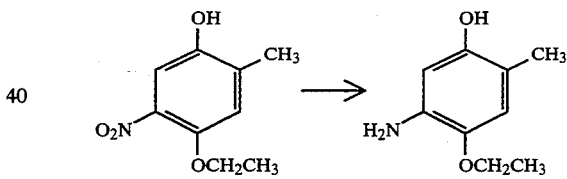

1.94 g (9.84 mmoles) 4-ethoxy-2-methyl-4-nitrophenol are dissolved in 20 ml ethanol and hydrated at room temperature over palladium/carbon. After the theoretical amount of hydrogen has been absorbed, the catalyst is removed by filtration and the filtrate is acidified with hydrochloric acid. After removing the solvent, 1.48 g (8.86 mmoles, 90 % of theory) of the product are obtained in the form of brown crystals which melt at 214° C. accompanied by decomposition.

$^1$H-NMR (D$_6$—DMSO)): δ=1.32 (t; J=6.9; —O—CH$_2$-CH$_3$)
2.10 (s; 3 H; Ar-CH$_3$)
4.02 (q; J=6.9 Hz; 2 H; —O—CH$_2$-CH$_3$)
6.93 (s; 1 H; 6-H)
6.97 (s; 1 H; 3-H)
9.4 (s; 1 H; OH; exchanged with D$_2$O)
9.89-9.99 ppm
(s; 2 H; NH$_2$; exchanged with D$_2$O)
MS (70 eV): m/e=167 (M+)

Example 4: 5-amino-4- (2'-hydroxyethyl) oxy-2-methylphenol

Step 1 and Step 2: see Example 2

Step 3: 4-(2'-hydroxyethyl)oxy-2-methyl-5-nitrophenol

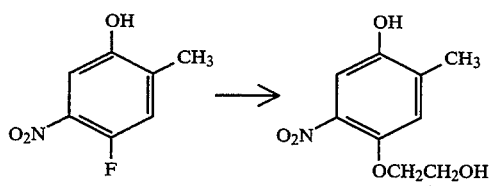

2.3 g (9.24 mmoles) 5-fluoro-2-mesyloxy-4-nitrotoluene are dissolved in a solution of 1.3 g KOH in 5 ml water and 50 ml 1,2-ethanediol and stirred at room temperature for 16 hours. The concentrated residue is absorbed in dichloromethane and chromatography is effected with silica gel in dichloromethane. 0.55 g (2.58 mmoles, 28 percent of theory) are obtained in the form of yellow crystals with a melting point of 150° C.

$^1$H-NMR (CDCl$_3$): δ=2.19 (s; 3 H; Ar-CH$_3$)
3.69 (m; 2 H, OCH$_2$—CH$_2$—OH)
4.06 (t; J=5 Hz; 2 H, OCH$_2$—CH$_2$—OH)
4.83 (s (wide); 1 H; OCH$_2$—CH$_2$—OH, exchanged with D$_2$O)
7.14 (s; 1 H; 3-H)
7.26 (s; 1 H; 6-H)
9.7 ppm (s (wide); 1 H; OH; exchanged with D$_2$O)
MS (70 eV): m/e=213 (M+)

Step 4:
5-amino-4-(2'-hydroxyethyl)oxy-2-methylphenol hydrochloride

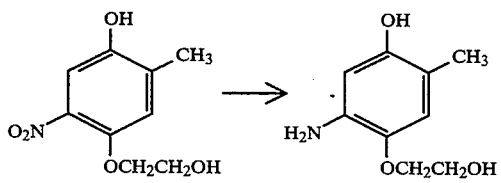

2.1 g (9.84 mmoles) of 4-(2'-hydroxyethyl)oxy-2-methyl-5-nitrophenol are dissolved in 20 ml ethanol and hydrated at room temperature over palladium/carbon. After the theoretical amount of hydrogen has been absorbed, the catalyst is removed by filtration and the filtrate is acidified with hydrochloric acid. After removal of the solvent, 1.62 g (8.86 mmoles, 90 percent of theory) of the product are obtained in the form of dark-brown crystals which melt at 183 to 185° C. accompanied by decomposition.

$^1$H-NMR (D$_6$—DMSO): δ=2.11 (s; 3 H; Ar-CH$_3$)
3.69 (m; 2 H; OCH$_2$CH$_2$OH
3.99 (t; J=4.6 Hz; 2H; OCH$_2$CH$_2$OH)
4.1–4.5 (s (wide); 1 H; OCH$_2$CH$_2$OH exchanged with D$_2$O)
6.93 (s; 1 H; 3-H)
6.94 (s; 1 H; 6-H)
9.45 (s (wide); 1 H; OH; exchanged with D$_2$O)
10.01 ppm (s (wide); 2 H; NH$_2$; exchanged with D$_2$O)
MS (70 eV): m/e=183 (M+) All $^1$H-NMR spectra (proton resonance spectra) indicated in the present application were made using a 300 megahertz $^1$H-NMR spectrometer (Bruker MW 300). The chemical shifts are given in ppm relative to the standard substance tetramethylsilane (TMS), where TMS=0ppm. Those in the indicated $^1$H-TMS=0ppm are given in ppm.

The abbreviations used in the indicated $^1$H-NMR data are as follows:

| | |
|---|---|
| s | singlet |
| d | doublet |
| t | triplet |
| q | quartet |
| m | multiplet |
| s (wide) | wide singlet |
| ppm | parts per million, one millionth of transmitting power |
| J | coupling constant |
| CDCl$_3$ | deuterochloroform |
| D$_6$-DMSO | deuterodimethylsulfoxide |

EXAMPLES FOR HAIR DYE COMPOSITION

Example A: Hair dye composition in gel form

| | |
|---|---|
| 0.22 g | 4-aminophenol |
| 0.37 g | 5-amino-4-fluoro-2-methylphenol hemisulfate |
| 0.30 g | ascorbic acid |
| 15.00 g | oleic acid |
| 7.00 g | isopropanol |
| 10.00 g | ammonia, 22 percent aqueous solution |
| 67.11 g | water |
| 100.00 g | |

50 g of the hair dye composition in gel form are mixed with 50 g hydrogen peroxide solution (6 percent) immediately before use, and the mixture is then applied to white human hair. After allowing it to act for a period of 30 minutes at 40° C., the dye substance is rinsed out with water, the hair is shampooed if necessary, rinsed with water and dried. The hair is dyed an intensive orange shade.

Example B: Hair dye solution

| | |
|---|---|
| 0.80 g | 4-aminophenol |
| 0.12 g | resorcinol |
| 0.10 g | m-aminophenol |
| 1.05 g | 5-amino-4-(2'-hydroxyethyl)oxy-2-methylphenol hydrochloride |
| 0.15 g | 2-amino-4-(2'-hydroxyethyl)aminoanisole hemisulfate |
| 0.05 g | 1-naphthol |
| 10.00 g | sodium lauryl alcohol diglycolic ether sulfate, 28 percent aqueous solution |
| 10.00 g | ammonia, 22 percent aqueous solution |
| 77.73 g | water |
| 100.00 g | |

50 g of this hair dye solution are mixed with 50 g hydrogen peroxide solution (6 percent) shortly before use and applied to blond human hair. The mixture is allowed to act for a period of 30 minutes at 40° C. The dye substance is then rinsed out with water, the hair is shampooed if necessary and dried. The hair is dyed a fashionable intensive gold-orange shade.

Example C: Hair dye composition in gel form

| | |
|---|---|
| 0.25 g | 4-amino-3-methylphenol |
| 0.45 g | 5-amino-4-ethoxy-2-methylphenol hydrochloride |
| 0.30 g | ascorbic acid |
| 15.00 g | oleic acid |
| 7.00 g | isopropanol |
| 10.00 g | ammonia, 22 percent aqueous solution |
| 67.00 g | water |

```
100.00 g
```

50 g of this hair dye composition in gel form are mixed with 50 g hydrogen peroxide solution (6 percent) shortly before use, the mixture is applied to white human hair and allowed to act for a period of 30 minutes at 40° C. The hair is rinsed with water, shampooed if necessary, and dried. The hair is dyed an intensive red shade.

Example D: Hair dye solution

```
2.26 g    4-aminophenol
0.95 g    4-amino-3-methylphenol
3.53 g    5-amino-2-ethyl-4-fluorophenol hemisulfate
1.28 g    2-amino-4-(2'-hydroxyethyl)aminoanisole sulfate
0.50 g    1-naphthol
10.00 g   sodium lauryl alcohol diglycolic ether sulfate,
          28 percent aqueous solution
10.00 g   ammonia, 22 percent aqueous solution
77.48 g   water
100.00 g
```

50 g of the above hair dye solution are mixed with 50 g hydrogen peroxide solution (6 percent) shortly before use. The mixture is applied to blond natural human hair and allowed to act for a period of 30 minutes at 40° C. The hair is then rinsed with water, shampooed if necessary and dried. The hair is dyed an intensive reddish-brown shade.

All of the percentages indicated in the present application are percent by weight unless otherwise indicated. We claim:

1. Composition for oxidative dyeing of hair containing 0.01 to 5.0 percent by weight of at least one coupler substance, said at least one coupler substance comprising at least one member selected from the group consisting of 5-aminophenol compounds of the formula

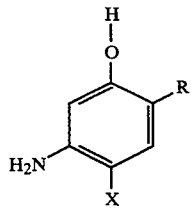
(I)

wherein R is an alkyl group having 1 to 4 carbon atoms, X is OR$^1$ and R$^1$ is selected from the group consisting of alkyl groups with 2 to 4 carbon atoms, monohydroxyalkyl groups with 2 to 4 carbon atoms and dihydroxyalkyl groups with 3 and 4 carbon atoms; and physiologically tolerated water-soluble salts thereof; and 0.1 to 6.0 percent by weight of a total amount of at least one developer substance and said at least one coupler substance, said at least one developer substance being selected from the group consisting of 1,4-diaminobenzene, 2,5-diaminotoluene, 2,5-diaminobenzyl alcohol, 2-(2'-hydroxyethyl)-1,4-diaminobenzene, 4-aminophenol, 4-amino-3-methylphenol, 4-amino-2-methoxymethylphenol, 4-amino-2-ethoxymethylphenol and tetraaminopyrimidine and physiologically tolerated water-soluble salts thereof.

2. Composition according to claim 1, wherein the at least one coupler substance is selected from the group consisting of 5-amino-4-ethoxy-2-methylphenol and 5-amino-4-(2'-hydroxyethyl)oxy-2-methylphenol.

3. Composition according to claim 1, wherein said at least one coupler substance further comprises a member selected from the group consisting of 1-naphthol, resorcinol, 4-chlororesorcinol, 4,6-dichlororesorcinol, 2-methylresorcinol, 2-amino-4-(2'-hydroxyethyl)-aminoanisole, 5-amino-2-methylphenol, 2,4-diaminophenoxyethanol, 4-amino-2-hydroxyphenoxyethanol, m-aminophenol, 3-amino-4-chloro-6-methylphenol, 3-amino-2-methylphenol, 4-hydroxy- 1,2-methylenedioxybenzene, 4-(2'-hydroxyethyl)amino-1,2-methylenedioxybenzene, 2,4-diamino-5-ethoxytolune, 2,4-diaminobenzyl alcohol, m-phenylenediamine, 4-hydroxyindole, 3-amino-5-hydroxy-2,6-dimethoxypyridine and 3,5-diamino-2,6-dimethoxypyridine and physiologically tolerated water-soluble salts thereof.

4. Composition according to claim 1, further comprising a member selected from the group consisting of 6-amino-2-methylphenol, 2-amino-5-methylphenol and 2-amino-5-ethoxyphenol.

5. Composition according to claim 1, further comprising at least one direct-dyeing dye selected from the group consisting of 4-((4'-amino-3'-methylphenyl)-(4''-imino-3''-methyl-2'', 5''-cyclohexadiene-1''-ylidene)-methyl)-2-methyl-aminobenzene monohydrochloride, 4-((4'-aminophenyl)-(4''-imino-2'',5''-cyclohexadiene-1''-ylidene)-methyl)-2-methylaminobenzene monohydrochloride, 2-nitro-1,4-diaminobenzene, 2-amino-4-nitrophenol, 2-amino-5-nitrophenol, 2-amino-4,6-dinitrophenol, 2-amino-5-(2'-hydroxyethyl)-aminonitrobenzene, 4-(2'-hydroxyethylamino)-3-nitrotoluene, 1-(2'-ureidoethyl)-amino-4-nitrobenzene, 7-(4'-aminophenylazo)-8-hydroxynaphthaline-4-sulfonic acid sodium salt, 1,4-diaminoanthraquinone and 1,4,5,8-tetraaminoanthraquinone and physiologically tolerated salts thereof.

6. Process of oxidative dyeing of hair, comprising mixing an oxidant with an amount of a hair dye composition according to claim 1 sufficient for dyeing of the hair to form a hair dyeing mixture, then applying the hair dyeing mixture to the hair, allowing the hair dyeing mixture to act on the hair at 15 to 50° C. for approximately 10 to 45 minutes, then rinsing the hair with water and drying.

7. Process as defined in claim 6, wherein the oxidant consists essentially of hydrogen peroxide.

8. A 5-aminophenol compound of the formula

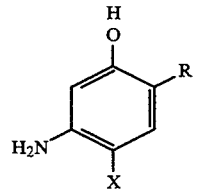
(II)

wherein R is an alkyl group having 1 to 4 carbon atoms, X is OR$^1$ and R$^1$ is selected from the group consisting of alkyl groups with 2 to 4 carbon atoms and monohydroxy alkyl groups with 2 to 4 carbon atoms and dihydroxyalkyl groups with 3 and 4 carbon atoms.

9. 5-amino-4-ethoxy-2-methylphenol.

10. 5-amino-4-(2'-hydroxyethyl)oxy-2-methylphenol.

11. Composition for oxidative dyeing of hair containing 0.010 to 5.0 percent by weight of at least one coupler substance, said at least one coupler substance comprising at least one member selected from the group consisting of 5-aminophenol compounds of the formula

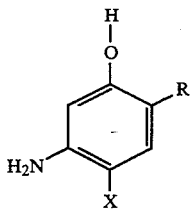

(I)

wherein R is an alkyl group having 1 to 4 carbon atoms and X is F; and physiologically tolerated water-soluble salts thereof; and 0.1 to 6.0 percent by weight of a total amount of at least one developer substance and said at least one coupler substance, said at least one developer substance being selected from the group consisting of 1,4-diaminobenzene, 2,5-diaminotoluene, 2,5-diaminobenzyl alcohol, 2-(2'-hydroxyethyl)-1,4-diaminobenzene, 4-aminophenol, 4-amino-3-methylphenol, 4-amino-2-methoxymethylphenol, 4-amino-2-ethoxymethylphenol and tetraaminopyrimidine and physiologically tolerated water-soluble salts thereof.

12. Composition according to claim 11, wherein the at least one coupler substance is selected from the group consisting of 5-amino-2-ethyl-4-fluorophenol and 5-amino-4-fluoro-2-methylphenol.

13. Composition according to claim 11, wherein said at least one coupler substance further comprises a member selected from the group consisting of 1-naphthol, resorcinol, 4-chlororesorcinol, 4,6-dichlororesorcinol, 2-methylresorcinol, 2-amino-4-(2'-hydroxyethyl)-aminoanisole, 5-amino-2-methylphenol, 2,4-diaminophenoxyethanol, 4-amino-2-hydroxyphenoxyethanol, m-aminophenol, 3-amino-4-chloro-6-methylphenol, 3-amino-2-methylphenol, 4-hydroxy-1,2-methylenedioxybenzene, 4-(2'-hydroxyethyl)amino-1,2-methylenedioxybenzene, 2,4-diamino-5-ethoxytolune, 2,4-diaminobenzyl alcohol, m-phenylenediamine, 4-hydroxyindole, 3-amino-5-hydroxy-2,6-dimethoxypyridine and 3,5-diamino-2,6-dimethoxypyridine and physiologically tolerated water-soluble salts thereof.

14. Composition according to claim 11, further comprising a member selected from the group consisting of 6-amino-2-methylphenol, 2-amino-5-methylphenol and 2-amino-5-ethoxyphenol.

15. Composition according to claim 11, further comprising at least one direct-dyeing dye selected from the group consisting of 4-((4'-amino-3'-methylphenyl) (4"-imino-3"-methyl-2", 5"-cyclohexadiene-1"-ylidene)-methyl)-2-methyl-aminobenzene monohydrochloride, 4-((4'-aminophenyl)-(4"-imino-2", 5"-cyclohexadiene-1"-ylidene)-methyl)-2-methyl-aminobenzene monohydrochloride, 2-nitro-1,4-diaminobenzene, 2-amino-4-nitrophenol, 2-amino-5-nitrophenol, 2-amino-4,6-dinitrophenol, 2-amino-5-(2'-hydroxyethyl)aminonitrobenzene, 4-(2'-hydroxyethylamino)-3-nitrotoluene, 1-(2'-ureidoethyl)-amino-4-nitrobenzene, 7-(4'-aminophenylazo)-8-hydroxynaphthaline-4-sulfonic acid sodium salt, 1,4-diaminoanthraquinone and 1,4,5,8-tetraaminoanthraquinone and physiologically tolerated salts thereof.

16. Process of oxidative dyeing of hair, comprising mixing an oxidant with an amount of a hair dye composition according to claim 11 sufficient for dyeing of the hair to form a hair dyeing mixture, then applying the hair dyeing mixture to the hair, allowing the hair dyeing mixture to act on the hair at 15 to 50° C. for approximately 10 to 45 minutes, then rinsing the hair with water and drying.

17. Process as defined in claim 16, wherein the oxidant consists essentially of hydrogen peroxide.

18. A 5-aminophenol compound of the formula

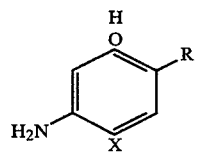

(II)

wherein R is an alkyl group having 2 to 4 carbon atoms and X is fluorine.

19. A 5-aminophenol compound as defined in claim 18, wherein the 5-aminophenol compound is 5-amino-2-ethyl-4-fluorophenol.

* * * * *